United States Patent [19]

Conner et al.

[11] 4,012,398

[45] Mar. 15, 1977

[54] QUATERNARY HALIDES OF MINK OIL AMIDES

[75] Inventors: Donald E. Conner, Clifton; Arnold W. Fogel, Park Ridge, both of N.J.

[73] Assignee: Van Dyk & Company, Incorporated, Belleville, N.J.

[22] Filed: Sept. 16, 1975

[21] Appl. No.: 613,965

[52] U.S. Cl. .............................. 260/404.5; 424/70; 424/316; 424/320
[51] Int. Cl.$^2$ .................... C11C 3/00; A61K 7/06; A61K 31/205; A61K 31/16
[58] Field of Search ........... 260/404.5; 424/70, 316

[56] References Cited

UNITED STATES PATENTS

| | | | |
|---|---|---|---|
| 2,282,702 | 5/1942 | Bock | 260/404.5 |
| 2,459,062 | 1/1949 | Cook et al. | 260/404.5 |
| 2,589,674 | 3/1952 | Cook et al. | 260/404.5 |
| 2,626,876 | 1/1953 | Carnes | 260/404.5 X |
| 2,930,761 | 3/1960 | Charret | 260/404.5 X |
| 2,954,325 | 9/1960 | Baumann | 424/70 X |
| 3,082,227 | 3/1963 | Sherr | 260/404.5 |

*Primary Examiner*—Winston A. Douglas
*Assistant Examiner*—William G. Wright

[57] ABSTRACT

Novel compositions of matter consisting of amido propyl dialkyl amino beta hydroxy ethyl ammonium halides of mink oil have been found to be excellent emollients having surprisingly good hair conditioning properties. They are prepared for example by reacting either ethylene chlorohydrin or ethylene bromohydrin in a medium of water and propylene glycol, with an amide obtained by reacting, under anhydrous conditions, mink oil with either dimethylaminopropylamine or diethylaminopropylamine using an alkaline catalyst such as sodium hydroxide.

5 Claims, No Drawings

QUATERNARY HALIDES OF MINK OIL AMIDES

FIELD OF THE INVENTION

There is an ever-increasing need for improved emollients, particularly those having superior hair conditioning properties in view of the increased emphasis on hair styling for fashion purposes. This invention provides novel synthetic cationic emollients having outstanding properties for the purposes mentioned.

DESCRIPTION OF THE PRIOR ART

Amido propyl dialkyl amino beta hydroxy ethyl ammonium halides of some of the individual fatty acid components of mink oil are known and in some cases have been tried as emollients. While some are effective for the latter general purpose, they have not exhibited satisfactory hair conditioning properties, particularly in providing requisite "body."

SUMMARY OF THE INVENTION

It has now been found that amido propyl dialkyl amino beta hydroxy ethyl ammonium halides of mink oil wherein the alkyl group is selected from the group consisting of methyl and ethyl, and the halide group is selected from the group consisting of chloride and bromide are excellent emollients and hair conditioning agents. This is particularly surprising since the corresponding amides formed from individual fatty acids contained in mink oil do not provide products of comparable superiority.

DISCUSSION OF PREFERRED EMBODIMENTS

The novel products of this invention may be prepared as follows.

Mink oil, a triglyceride, is reacted with either gamma dimethylamino or gamma diethylaminopropylamine at between about 140°–160° C. using an alkaline catalyst and a nitrogen atmosphere which inhibits oxidation of the unsaturated fatty acids present in mink oil. It has been found that alkaline catalyst such as sodium hydroxide, potassium hydroxide and sodium methylate or ethylate work equally well.

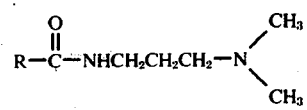

Formula I

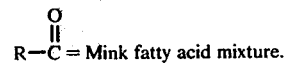

R—C = Mink fatty acid mixture.

The above mink amide of Formula I is quaternized with either ethylene chlorohydrin or ethylene bromohydrin at about 105°–115° C. in a solvent mixture of water and propylene glycol. This solvent mixture is used to control the reaction temperature and thus avoid decomposition of the quaternary as it is formed.

The compositions of this invention are thus represented in Formula II below.

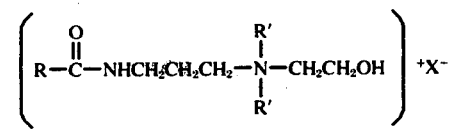

Formula II

In this formula RCO represents the mink oil fatty acid mixture, and R' and R' are alkyl groups having 1 or 2 carbon atoms which can be the same or different, and X is chloride or bromide. They are water soluble, can act as secondary emulsifiers, and have unusually good eye irritation characteristics.

The mink oil utilized is a well known material of cosmetic chemistry. Typical specifications and constituents are tabulated directly below.

| TYPICAL PROPERTIES AND SPECIFICATION RANGE - EMULAN MULTI-REFINED OIL OF MINK | | | |
|---|---|---|---|
| | EMULAN SAMPLE No. MW-033071-(1) | SPECIFICATION RANGE | REFERENCE |
| CLARITY | CLEAR WHEN RECONSTITUTED | CLEAR WHEN RECONSTITUTED | (1,2,3) |
| COLOR | LIGHT AMBER | LIGHT AMBER | |
| A. Lovibond 5¼"Col. | R- 0.9 Y- 9.0 | R- 0.6 – 3.9 Y- 9.0 – 35.0 | (2) |
| ODOR | BLAND | BLAND | |
| SAPONIFICATION NUMBER | 197.8 | 194 – 208 | (2,3) |
| ACID NUMBER | 0.30% | 0.1 – 0.4% | (2,3) |
| REFRACTIVE INDEX | 1.4650 | 1.4650 – 1.4670 | (3) |
| CLOUD POINT | 29° F. | 29° – 32° F. | (1,2) |
| POUR POINT | 27° F. | 27° – 30° F. | (1,2) |
| MOISTURE | 0.11% | 0.11 – 0.18% | (2) |
| POUNDS PER GALLON | 7.9 | 7.9 | (3) |
| SPECIFIC GRAVITY | 0.906 | 0.906– 0.915 | (3) |
| UNSAPONIFIABLE MATTER | 0.17% | 0.10 – 0.2% | (2) |
| STERIODS-(Natural) | | 0.15 – 0.2% | (3) |
| COLESTEROL | 0.15% | | |
| IODINE VALUE | 93.5 | 76.7 – 95 | (2,3) |
| VISCOSITY (Ostwald) | 50 cps. at 29° C. | 50 cps. at 29° C. | (3) |
| SURFACE TENSION | 31.0 dyne cm. at 29° C. | 31.0 dyne cm at 29° C. | (3) |
| MICRO-ORGANISM COUNT | Less than 10 per gram | Less than 10 per gram | (3) |
| FATTY ACID COMPOSITION-RANDOM SAMPLES OF EMULAN | | | |

REFERENCES
1. EMLIN INCORPORATED
2. AMERICAN MEAT INSTITUTE SERVICE LABORATORY
3. J. M. CROSS (RUTGERS)

TYPICAL PROPERTIES AND SPECIFICATION RANGE EMULAN MULTI-REFINED OIL OF MINK

|  | Ref. No. 1 Specification Range | Ref. No. 3 EMULAN - MW-033071-(1) |
|---|---|---|
| Myristic | 3.1 – 3.5% | 4.8% |
| Myristoleic | 0.9 – 1.0% | |
| Palmitic | 16.4 – 19.0% | 12.2% |
| Palmitoleic | 15.2 – 18.0% | 22.2% |
| Stearic | 2.6 – 3.6% | 9.1% |
| Oleic | 42.7 – 47.1% | 37.1% |
| Linoleic | 10.0 – 13.1% | 12.3% |
| Linolenic | 1.0 – 2.0% | |
| Behenic | Trace | |
| Erucil | Trace | |
| Octatetraenoic | | 2.3% |

COMPARISON OF HUMAN FAT AND EMULAN MULTI-REFINED OIL OF MINK

|  | HUMAN FAT* | EMULAN |
|---|---|---|
| Sp. Gravity | 0.917 | 0.906 – 0.915 |
| Refractive Index | 1.4709 | 1.4650 – 1.4670 |
| Iodine Value | 66.8 | 76.7 – 95.0 |
| Saponification Value | 199 | 194 – 208 |
| Unsaponifiable Matter | 0.3% | 0.1 – 0.3% |
| Solidifying point of Fatty Acids | 30° F. | 29° F. |

*TECHNOLOGY & ANALYSIS OF FATS AND OILS
J. Lewkowitsch - McMillian & Company Ltd., London
6 Edition, Vol. 2, Page 696

The improved properties of the materials of this invention are believed to stem from the inherent mixture of fatty acid components contained in the mink oil. Thus the specific mink oil utilized is not critical.

This invention, product work-up and properties of these novel materials will be better understood by reference to the following examples.

EXAMPLE 1

Preparation of the Dimethyl Chloride Derivative

Part A (Preparation of the dimethylaminopropylamide of mink oil)

138 parts mink oil;
49 parts gamma dimethylaminopropylamine;
0.5 parts potassium hydroxide.

The above materials were heated in a 1000 ml. reaction flask, fitted with an agitator, condenser, thermometer, nitrogen sparge tube and a heating mantle to 140°–150° C. for 8 hours. The alkali number at this point was 160. After cooling to 60° C., the following materials were added in the order given:

Part B 150 parts propylene glycol;
125 parts water;
39 parts ethylene chlorohydrin.

This mixture was heated at 109°–111° C. for 10 hours. An ionic chloride of 3.6% was obtained (theoretical chloride is 3.6%). The final composition of the above reaction mixture was found to contain:

42% quaternary salt;
3% glycerol;
30% propylene glycol;
25% water.

EXAMPLE 2

Preparation of Diethyl Bromide Derivative

Part A (Preparation of the gamma diethylaminopropylamide of mink oil)

138 parts mink oil;
62.5 parts gamma diethylaminopropylamine;
0.3 parts sodium hydroxide.

The above materials were heated in a 1000 ml. reaction flask; fitted with an agitator, condenser, thermometer, nitrogen sparge tube and heating mantle for 10 hours at 145°–155° C. The resulting amide had an alkali number of 154.

Part B (Formation of quaternary bromide of the above amide)

After cooling to 60° C., the following materials were added in the order given:

174.3 parts propylene glycol
145.2 parts water
60.6 parts ethylene bromohydrin

A maximum value of 6.6% ionic bromide was obtained after heating at 110°–115° C. for 12 hours. (6.7% bromide theory)

The resulting mixture had the following composition:
42% quaternary salt;
3% glycerol;
30% propylene glycol;
25% water.

EXAMPLE 3

Preparation of Dimethyl Bromide and Diethyl Chloride Derivatives

The dimethyl bromide and the diethyl chloride derivatives are prepared as indicated in Examples 1 and 2 by varying the reagents.

EXAMPLE 4

Identical compositions as those of this invention were prepared except instead of using mink oil as a starting material, the following individual acid components were utilized: lauric, myristic, palmitic, oleic and stearic. These component compounds were then evaluated against the mink oil compositions in clear after-shampoo hair conditioners and lotion hair conditioners. The results are tabulated on the following page.

It should be noted that the mink oil compositions of this invention are better in some cases with regard to solubility, in others with regard to emulsifiability, in all cases better with regard to overall hair conditioning and sometimes better with regard to all three forementioned properties.

|  | Clear Conditioner | | | |
|---|---|---|---|---|
|  | Solubility (Clarity at 25° C.) | Anti-Tangle | Anti-Static | Overall Hair Condition |
| Mink oil | Clear | Yes | Yes | Excellent |
| Lauryl derivative | Clear | None | None | Dry & Scroopy |
| Myristyl derivative | Clear | Some | Some | Dry |
| Palmityl derivative | Cloudy at 5–10° C. (Doesn't clear & Precipitate | Some | Some | Fair |
| Oleyl derivative | Cloudy at 25° C. | Some | Some | Oily same day |
| Stearyl derivative | Cloudy at 5–10° C. | Yes | Yes | Oily next day |

|  | Lotion Conditioner | | | |
|---|---|---|---|---|
|  | Emulsion Stability 25 & 45° C. | Anti-Tangle | Anti-Static | Overall Hair Condition |
| Mink oil | Excellent | Yes | Yes | Excellent |
| Lauryl derivative | Separation (thin lotion) | No | No | Fair (from esters) |
| Myristyl derivative | } | Some | Some | Fair (from esters) |
| Palmityl derivative | All turn lotion | Some | Some | Fair (from esters) |
| Oleyl derivative | formula into "cream", | Some | Some | Oily |
| Stearyl derivative | too thick! | Yes | Yes | Oily next day |

EXAMPLE 5

Typical formulations employing the products of this invention are listed below where Ceraphyl 5 connates these products, and the other trademark materials are either well known or source described.

| Lotion hair conditioner (lotion balsam type) | | pH 3.7 |
|---|---|---|
| Phase A: | Ceraphyl 28 (5) | 2.0 |
|  | Ceraphyl IPL | 2.0 |
|  | Cerasynt SD | 4.0 |
|  | Myrj 52 (1) | 1.0 |
|  | Promulgen D (2) | 2.0 |
|  | Cetyl Alcohol | 1.0–1.5 (n) |
| Phase B: | Water, deionized | 83.8–83.3 |
|  | Cellosize OP 30,000 (3) | 0.3 |
|  | Ceraphyl 60 | 1.0 |
|  | Ceraphyl 65 | 2.5 |
|  | Lactic Acid | 0.3 |
|  | BTC 2125M (4) | 0.1 |
| Phase C: | Color and Perfume Oil V-2374/2 | q.s. |
|  |  | 100.0% |

(n) the more cetyl alcohol used, the higher the final viscosity.
(1) ICI America Incorporated
(2) Robinson Wagner
(3) Union Carbide
(4) Onyx Chemical Company
(5) Van Dyk & Company, Inc.

Procedure

Completely pre-disperse Cellosize in water and add the rest of ingredients of Phase B. Heat both Phases to 80° C. Add slowly Phase A to Phase B with constant agitation at 80° C. and cool to 50° C. continuing agitation (avoid aeration and reduce speed of mix as lotion cools). Add color and perfume, continue cool & slow mix to 25°–28° C.

Directions for Use

Use app. ½ oz. after shampoo. Massage throughout wet hair, leave on for one minute, then rinse off.

| Clear after shampoo conditioner | | pH 4.8 |
|---|---|---|
| Phase A: | Cellosize QP 30,000[1] | 0.30 |
|  | Water, deionized | 92.50 |
| Phase B: | Ceraphyl 65 | 2.50 |
|  | Ethanol (SD 40, Anhyd.) | 2.50 |
|  | Standapol OLB 50[2] | 1.00 |
|  | Perfume (Solubilized if necessary) | q.s. |
| Phase C: | Ceraphyl 60 | 1.00 |
|  | Citric Acid (30% Aq.) | 0.10 |
|  | BTC 2125M[3] | 0.10 |
|  |  | 100.0% |

[1] Union Carbide Corporation
[2] Henkel Incorporated
[3] Onyx Chemical Company

Procedure

Disperse Cellosize in water, till thoroughly dispersed, and at the same time, mix Phase B until clear. Add Phase B into Phase A with constant agitation, then add Phase C. Mix until uniform.

Directions for use

Use app. ½ oz. after shampoo. Massage foam throughout wet hair for a minute, then rinse off.

The products of this invention can thus be used as emulsifiers and conditioners for a wide variety of topical applications.

The advantages of this invention will be apparent to the skilled in the art. Safe hair conditioning agents of unique properties are provided from a readily available source material, mink oil. The superior properties of the claimed materials far exceed those derived from the individual acids of the oil.

It will be understood that this invention is not limited to the specific examples which have been offered as particular embodiments, and that modifications can be made without departing from the spirit thereof.

What is claimed is:

1. As novel compositions of matter, amido propyl dialkyl amino beta hydroxy ethyl ammonium halides of mink oil having the formula

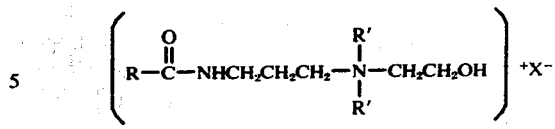

wherein RCO is the mink oil fatty acid mixture, R' is an alkyl group of 1–2 carbon atoms, and X is a halide selected from the group consisting of chloride and bromide.

2. The composition of claim 1 in which the alkyl is ethyl and the halide is chloride.

3. The composition of claim 1 in which the alkyl is ethyl and the halide is bromide.

4. The composition of claim 1 in which the alkyl is methyl and the halide is chloride.

5. The composition of claim 1 in which the alkyl is methyl and the halide is bromide.

* * * * *